United States Patent
Hertweck

(10) Patent No.: US 8,439,874 B2
(45) Date of Patent: May 14, 2013

(54) APPARATUS AND METHOD FOR CONTROLLING A VACUUM SOURCE TO ESTABLISH FLUID FLOW

(75) Inventor: David Hertweck, Valley Park, MO (US)

(73) Assignee: Bausch & Lomb Incorporated, Rochester, NY (US)

(*) Notice: Subject to any disclaimer, the term of this patent is extended or adjusted under 35 U.S.C. 154(b) by 751 days.

(21) Appl. No.: 12/275,875

(22) Filed: Nov. 21, 2008

(65) Prior Publication Data

US 2010/0130929 A1    May 27, 2010

(51) Int. Cl.
*A61M 1/00* (2006.01)
(52) U.S. Cl.
USPC .............................. 604/118; 604/30
(58) Field of Classification Search .................... 604/118
See application file for complete search history.

(56) References Cited

U.S. PATENT DOCUMENTS

| | | | |
|---|---|---|---|
| 4,592,741 A * | 6/1986 | Vincent | 604/35 |
| 5,733,256 A | 3/1998 | Costin | |
| 5,747,824 A * | 5/1998 | Jung et al. | 250/577 |
| 6,599,277 B2 | 7/2003 | Neubert | 604/317 |
| 6,634,237 B2 | 10/2003 | Neubert | 73/861.12 |
| 7,524,299 B2 * | 4/2009 | Hopkins et al. | 604/30 |
| 7,563,242 B2 * | 7/2009 | Yaguchi et al. | 604/43 |
| 2008/0114372 A1 | 5/2008 | Edwards | |

FOREIGN PATENT DOCUMENTS

| | | |
|---|---|---|
| JP | H5-23394 | 2/1993 |
| WO | WO 93/18802 A1 | 9/1993 |
| WO | WO 03/047653 A1 | 6/2003 |
| WO | WO 2007/001503 A2 | 1/2007 |

OTHER PUBLICATIONS

International Search Report (PCTISA/210) and Written Opinion (PCT/ISA/237) mailed on Mar. 1, 2010.

* cited by examiner

*Primary Examiner* — Laura Bouchelle
*Assistant Examiner* — Weng Lee
(74) *Attorney, Agent, or Firm* — Jeffrey B Powers

(57) ABSTRACT

A flow control system that includes a vacuum device configured to control the level of vacuum applied for urging the flow of aspirated fluid from a surgical site, and a vacuum sensor configured to communicate a signal representative of the sensed vacuum level. A flow sensor control is configured to generate a signal indicative of the rate of aspirated fluid flow. A flow controller monitors the vacuum sensor and the flow measurement device, and communicates a requested vacuum level to the vacuum device for establishing a desired vacuum level. The flow controller employs a first feed back loop that compares the actual sensed vacuum level with the requested vacuum level and adjusts the requested vacuum level as needed. The flow controller implements a second feedback loop that compares the actual flow rate of aspirated fluid with a desired flow rate, and adjusts the requested vacuum level to achieve the desired flow rate.

6 Claims, 3 Drawing Sheets

APPARATUS AND METHOD FOR CONTROLLING A VACUUM SOURCE TO ESTABLISH FLUID FLOW

FIELD

The present invention relates to sensing an aspiration flow rate in a surgical pump system. More particularly, the present application is directed towards flow measurement in ophthalmic microsurgical pump systems.

BACKGROUND

The statements in this section merely provide background information related to the present disclosure and may not constitute prior art.

The flow rate of fluids through an aspiration tube is of interest in ophthalmic surgical operations. During ophthalmic microsurgery, small probes are inserted into an operative site to remove tissues. Infusion fluids may be infused into the operative site through the probes, and may also be aspirated from the site. Surgical cassettes may also be coupled to surgical probes, to provide for collection of aspirated fluids. Measurement of the surgical aspiration flow rate may be valuable, in that it can be used to help control the ophthalmic surgical equipment. However, where vacuum-pump or venturi-based vacuum systems are employed for establishing aspiration flow, control of the vacuum source can make regulation of aspiration flow rate difficult to achieve. Therefore, it would be desirable to incorporate a vacuum control system that can more effectively control or regulate aspiration flow rate.

SUMMARY

The present disclosure relates to ophthalmic surgical systems in which an aspiration flow measurement system is provided. According to one embodiment of an aspiration flow control system, a flow control system is provided for regulating the rate of aspirated fluid flow from a surgical site. The flow control system includes a vacuum generating device that is configured to control the level of a vacuum applied for urging the flow of aspirated fluids from a surgical site, and a vacuum sensor configured to communicate a signal representative of the level of the vacuum being applied. The system further includes a flow measurement device that is configured to generate a signal indicative of the rate of aspirated fluid flow. The system is controlled by a flow controller that monitors both the vacuum sensor and the flow measurement device. Based on feedback from the vacuum sensor and flow measurement device, the system communicates a requested vacuum level to the vacuum device, to establish a desired vacuum level. The flow controller is configured to implement a first feed back loop that compares the requested vacuum level with the actual sensed vacuum level, and adjusts the requested vacuum to maintain the desired vacuum level. The flow controller is further configured to implement a second feedback loop that compares the sensed aspiration flow rate with a desired aspiration flow rate and adjusts the requested vacuum communicated to the vacuum device, to thereby achieve the desired aspiration flow rate.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
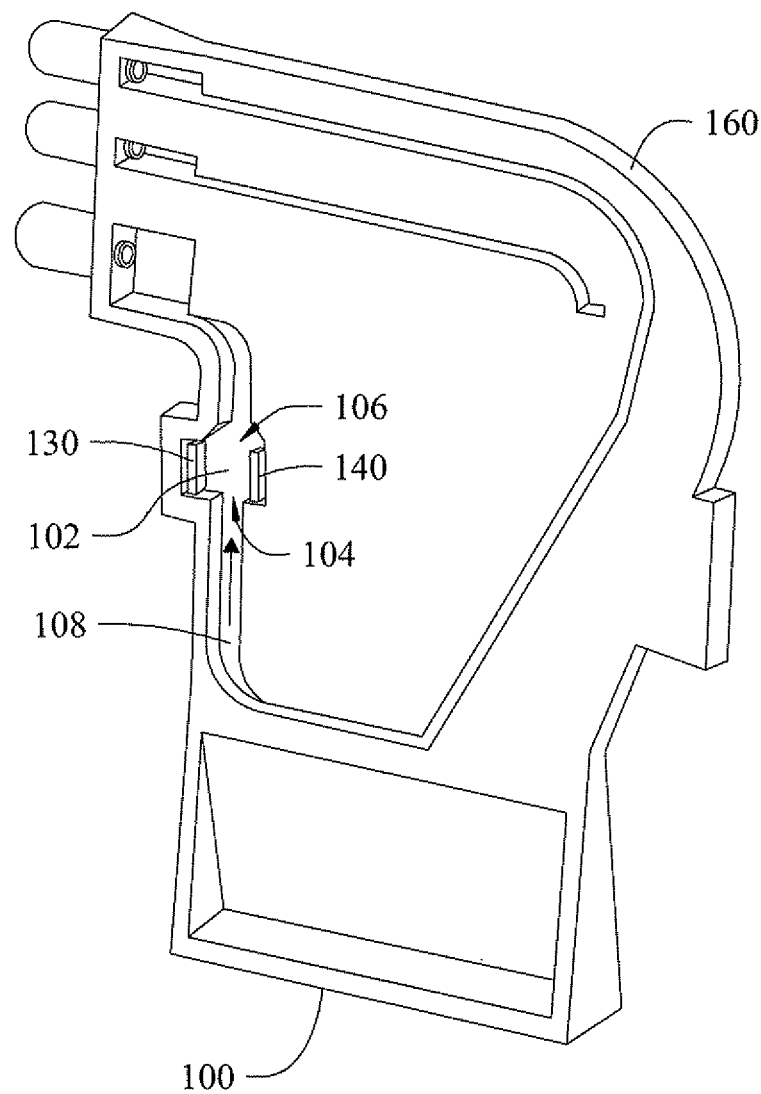
FIG. 1 is a cut-away perspective view of a portion of a flow sensing device for an ophthalmic surgical system, in accordance with the principles of the present disclosure.

The following description is merely exemplary in nature and is not intended to limit the present disclosure, application, or uses. It should be understood that throughout the drawings, corresponding reference numerals indicate like or corresponding parts and features.

In the various embodiments, a flow control system for sensing and controlling vacuum-based aspiration fluid flow is provided for an ophthalmic microsurgical system. The flow control system generally comprises a vacuum device that is configured to control the level of a vacuum applied for urging the flow of aspirated fluids from a surgical site. The flow control system includes a vacuum sensor that is configured to communicate a signal representative of the sensed vacuum level that is being applied. The system further includes a flow measurement device that is configured to generate a signal indicative of the rate at which fluid flow is aspirated from the surgical site. The ophthalmic system is controlled by a flow controller that monitors the vacuum sensor and the flow measurement device, and communicates a requested vacuum level to the vacuum device, to thereby establish a desired vacuum level. The flow controller may be configured to implement a first feed back loop that compares the requested vacuum level with the actual sensed vacuum level, and adjusts the requested vacuum level, to achieve the desired vacuum level. The flow controller is further configured to implement a second feedback loop that compares the sensed aspiration flow rate with a desired aspiration flow rate, and adjusts the requested vacuum level to achieve a desired aspiration flow rate.

Referring to FIG. 1, one example of an aspiration flow measurement control device for an ophthalmic surgical system is shown. The aspiration flow measurement device may be incorporated into a cassette within an ophthalmic surgical system, or may be provided as a separate device. In the various embodiments of a flow control system for an ophthalmic system, the system includes a flow measurement device that is configured to generate a directly measured signal indicative of the flow rate of fluid aspirated from a surgical site, such as an eye, for example.

The signal from the flow measurement device representing the aspirated fluid flow rate may be compared to a desired flow rate, to provide a means of feedback for controlling the rate of aspirated fluid flow. The sensed flow rate signals are preferably input to a flow controller, which responsively determines whether to increase or decrease the flow rate. As shown in FIG. 1, the aspirated fluid flow measurement device comprises a partial housing 100, which includes an electrode terminal chamber 102 having an inlet 104 and an outlet 106. The inlet 104 to the electrode terminal chamber 102 is in communication with a flow channel 108, which communicates the flow of aspirated fluids, such as an electrically conductive saline solution, for example. The electrode terminal chamber 102 further includes first and second electrode terminals 130 and 140 that are arranged opposite one another in a spaced-apart relationship. The electrode terminals provide for generating at least one electrical signal indicative of the flow rate of the aspirated fluid flowing through the electrode terminal chamber 102.

Figure 2:
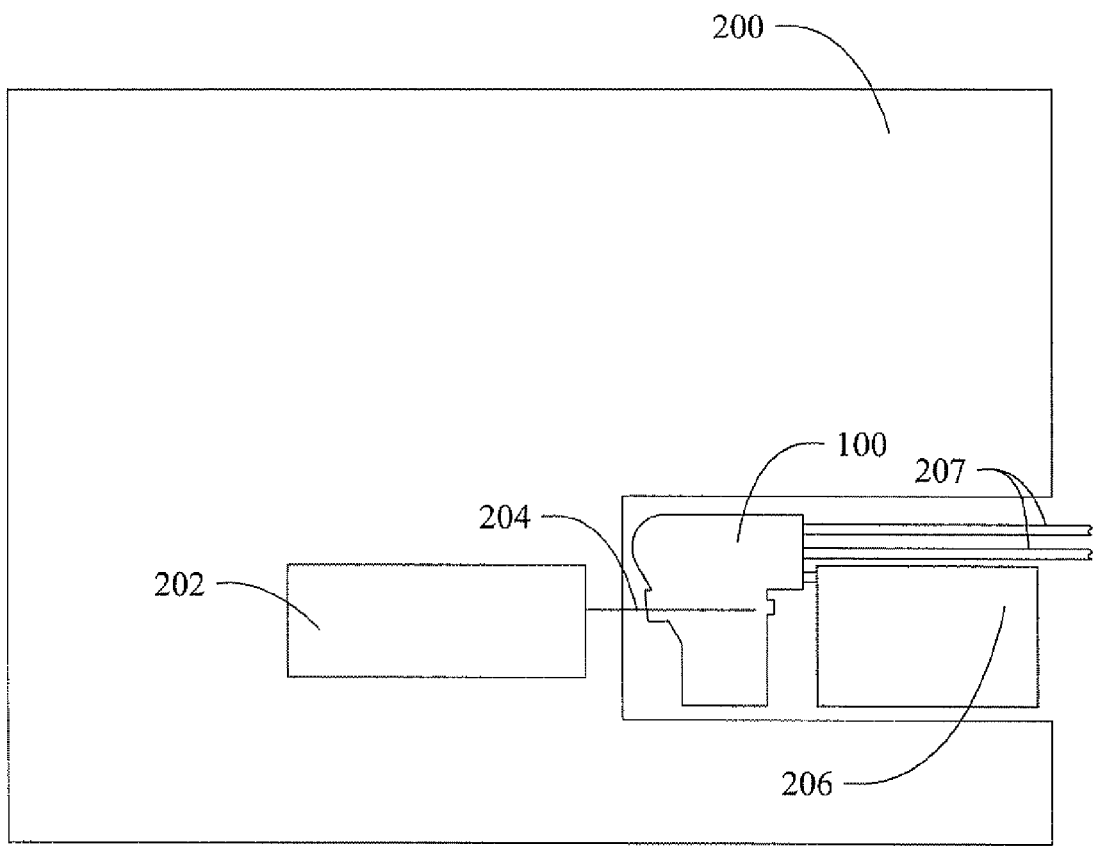
FIG. 2 shows a schematic view of a console including a flow controller and an aspiration flow measurement sensor according to the principles of the present disclosure.

The flow of fluids through terminal chamber of housing 100 can be detected by, for example, a hall-effect sensor that may be part of or associated with a flow sensor console 200, as shown in FIG. 2. The aspirated fluid that flows through the housing 100 is preferably received within a collection cassette 206 via aspiration lines 207, at least one of which is connected to a surgical instrument (not shown). The hall-effect sensor, which ideally is operatively positioned relative to the electrodes 130 and 140, is not shown in FIG. 1, but is described in U.S. Pat. Nos. 6,599,277 and 6,634,237, both of which are assigned to the current assignee of the present application, and are incorporated herein by reference.

As shown in FIG. 2, the electrodes disposed within the flow measurement device 100 and the hall-effect sensor may be connected to a flow sensor control 202 via a wire or electrical connection 204, for example. Preferably, the flow sensor control 202 is configured to provide a time-averaged flow rate signal based on signals from the flow measurement device 100 that are received at a predetermined rate within a given period of time. The flow sensor control 202 receiving the signals utilizes the flow measurement information to obtain the actual sensed flow rate, which may be compared to a desired flow rate as part of a feedback control loop for controlling the rate of aspirated fluid flow.

The flow control system also includes a vacuum sensor configured to communicate a signal representative of the actual level of vacuum being applied to establish flow of aspirated fluid. The vacuum sensor may be configured to sense the level of negative pressure, or the level of the vacuum that is being applied by the vacuum source. The vacuum level may be used to monitor and adjust the flow of aspirated fluid from the surgical site. The vacuum sensor provides a signal that is communicated to a flow controller, which uses the signal to determine whether to increase or decrease the level of vacuum being applied by the vacuum source, to thereby adjust the flow rate of aspirated fluid.

Figure 3:
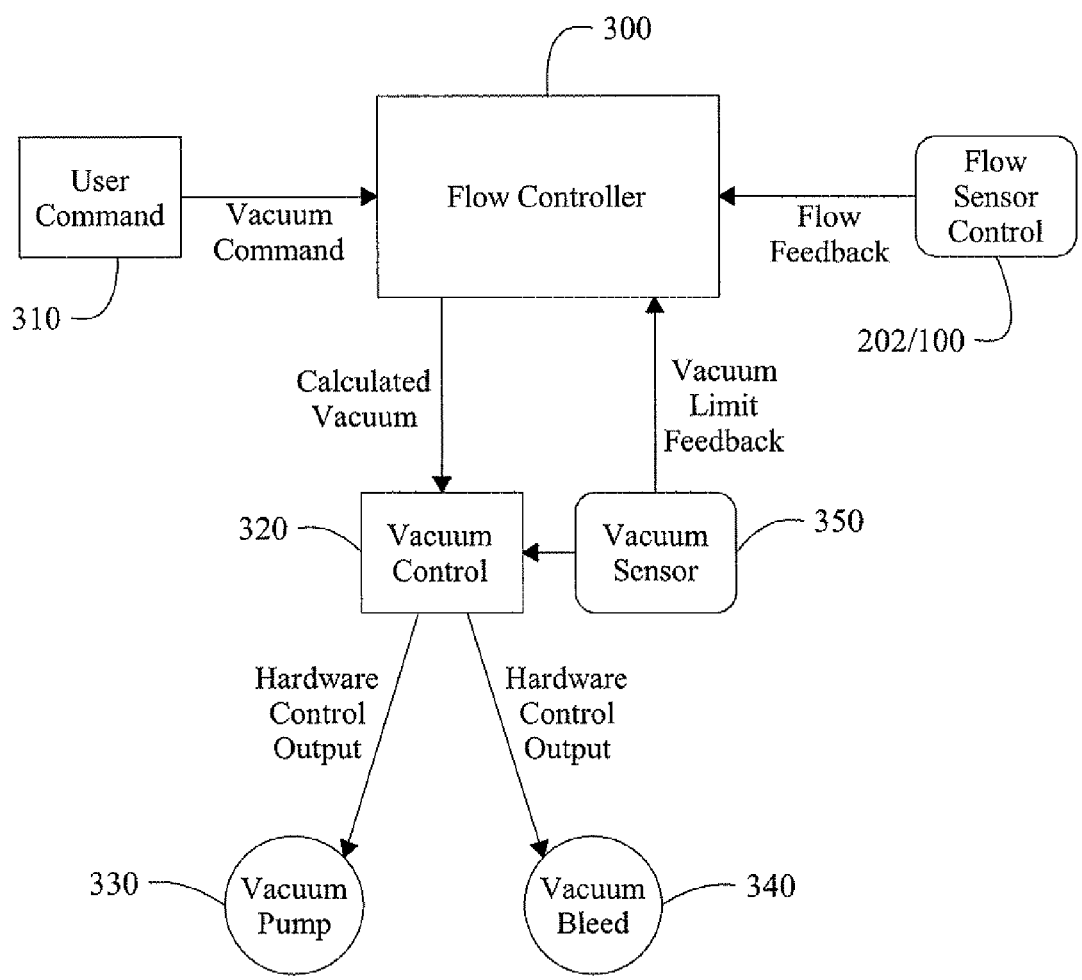
FIG. 3 shows a functional block diagram of a flow control system for sensing and controlling vacuum-based aspiration fluid flow in accordance with the principles of the present disclosure.

Referring to FIG. 3, one embodiment of a flow control system according to the principles of the present disclosure is shown in a block diagram. The flow control system comprises a flow controller 300 that is in communication with various sensors and control devices, including a vacuum device that is configured to control the level of a vacuum being applied for urging the flow of aspirated fluid from a surgical site.

Included in the flow control system is a flow sensor or flow measurement device 202, which is configured to generate a signal indicative of the rate of aspirated fluid flow. This flow measurement signal is communicated to the flow controller 300. It is noted that the flow sensor 202 may be a flow sensor device of the type shown in FIGS. 1 or 2, or alternatively, the device may be a simple analogue output flow sensing component. The flow sensor 202 is configured to provide an output signal that is indicative of the sensed flow rate of aspirated fluid from a surgical site, such as an eye, for example.

The flow control system also includes a vacuum sensor 350 for providing a signal that represents the sensed vacuum level or negative pressure, which signal is communicated to the vacuum control device 320, or to flow controller 300. The vacuum sensor 350 may be a vacuum transducer, for example, that provides an output signal indicative of the level of the vacuum being applied. The output of vacuum sensor 350 may be used to determine a time averaged vacuum level based on periodic sampling of the transducer output signal. The sensed vacuum level information may then be compared to the requested vacuum level, for determining whether to increase or decrease the requested vacuum level. This provides a feedback means for adjusting the vacuum generating device to increase or decrease the vacuum level that is being applied.

The flow control system further comprises a vacuum source or vacuum generating device (collectively 330 and 340). The vacuum device is configured to control the vacuum level being applied for urging the flow of aspirated fluids from a surgical site, based on the vacuum level that is being requested. The flow control system further comprises a vacuum control 320 that controls the vacuum generating device to regulate the vacuum level. The vacuum control 320 is configured to receive a signal from the flow controller 300 that includes the requested vacuum level to be applied, and the vacuum control 320 is also configured to receive signal information from the vacuum sensor 350 that is indicative of the sensed vacuum level. Based on the sensed vacuum level, the vacuum control 320 adjusts the vacuum being generated, to thereby maintain the vacuum level requested by the flow controller 300. The vacuum control 320 accordingly may generate a vacuum level based on the sensed vacuum level, to achieve the requested vacuum communicated by the flow controller 300.

It should be noted that the flow control system may employ different types of vacuum sources. For example, the vacuum source could be in the form of a venturi-based system in communication with a pressurized air source, which supplies pressurized air to a venturi for establishing a vacuum at a venturi port. In such a system, the vacuum level established by the venturi may be adjusted by a vacuum bleed 340. For example, a proportional valve may be used to adjust the flow of pressurized air to the venturi, to establish a desired vacuum level. Such adjustment may be achieved by providing an electrical signal to the proportional bleed valve 340. For purposes of this disclosure the term "vacuum pump" should be taken to include the use of a venturi source.

The vacuum source could also comprise a vacuum pump 330, such as a rotary vane or other suitable pump that generates a vacuum. The vacuum control 320 may be configured to adjust the vacuum level generated by the pump 330 by adjusting an electrical signal to the pump 330, where the vacuum generated varies based on the electrical signal. It should be understood that the vacuum control 320 may be configured to communicate an electrical signal to different vacuum sources, and to vary the electrical signal based on the sensed vacuum level obtained from the vacuum sensor 350. Accordingly, the vacuum control 320 may provide a signal to the vacuum source for maintaining a desired vacuum level requested by the flow controller 300. In this example, a vacuum bleed 340 may also be used to refine the desired vacuum level.

The flow control system further includes a user command 310 that allows a surgeon to input, select, or adjust the level of the vacuum being applied, to thereby establish a desired flow rate of aspirated fluid. The flow controller 300 receives information from the flow sensor 202 and the vacuum sensor 350 for determining a sensed vacuum level and sensed flow rate of aspiration fluid. The flow controller 300 compares the sensed flow rate information to the desired vacuum level or vacuum command received via an input device of the user command 310.

The flow controller is configured to implement a first feed back loop that compares the actual sensed vacuum level with the requested vacuum level, and adjusts the requested vacuum as needed to achieve the desired vacuum level. Accordingly, the first feedback control loop provides for controlling the vacuum level to achieve the requested vacuum level. Control may be achieved via the vacuum control by adjusting air flow under pressure to a venturi. Alternatively, control may be provided via the vacuum control by adjusting an electrical signal to a vacuum pump.

However, where vacuum-pump or venturi-based vacuum systems are employed for establishing flow of aspirated fluid, control of the vacuum source can make regulation of aspirated fluid flow difficult to achieve. For example, where the flow controller 300 determines a calculated vacuum level for establishing a desired rate of aspirated fluid flow, the resulting flow rate could be adversely affected by a change in conditions that may occur during a surgical procedure, such as a restriction caused by tissues aspirated into the flow path. Such an occurrence could result in the reduced flow of fluids aspirated from the surgical site, which may cause an undesirable increase in pressure at the site and cause injury to the subject.

To address the above risk, the flow controller 300 is configured to utilize a second feedback control loop for controlling the flow rate of aspirated fluid. The flow controller 300 is configured to employ the second feedback control loop to monitor the output from the aspiration flow sensor 202, and to adjust the vacuum level requested of the vacuum control 320 (or of the vacuum source), which was determined by the first feedback loop.

Accordingly, the flow controller 300 is configured to receive from the user command 310 an input of a desired vacuum command or vacuum level, and to output a calculated or requested vacuum level signal to the vacuum control 320. The vacuum control 320 monitors a vacuum sensor, and responsively provides an output signal to venturi or vacuum pump 330 and a vacuum bleed 340 to establish the requested vacuum level communicated by the flow controller 300.

The sensed vacuum level may then be monitored by the vacuum control 320 for adjusting the vacuum source to achieve the requested vacuum level, as part of a first feedback control loop for controlling the desired vacuum level. The flow controller 300 is further configured to utilize the second feedback loop that compares the sensed flow rate of aspirated fluid with a desired flow rate, and adjusts the requested vacuum level being communicated to the vacuum control device 320, to thereby achieve the desired flow rate of aspirated fluid. Accordingly, the flow controller 300 may employ first and second control loops for controlling the level of vacuum being applied to effect the flow of aspirated fluids, to thereby control the flow rate of aspirated fluid from a surgical site.

From the above, it may be appreciated that the present invention provides an improvement to flow control of aspirated fluid, in monitoring both a vacuum sensor and a flow sensor for controlling the vacuum level and flow rate of fluid aspirated from a surgical site. The present invention is illustrated herein by example, and various modifications may be made by a person of ordinary skill in the art. While the apparatus and methods shown or described above have been characterized as being preferred, various changes and modifications may be made therein without departing from the spirit and scope of the invention as defined in the following claims.

What is claimed is:

1. An aspiration flow control system for an ophthalmic microsurgical system comprising:
 a vacuum device configured to control the level of a vacuum applied for establishing the flow of aspirated fluid from a surgical site;
 a vacuum sensor configured to communicate a signal representative of the sensed level of the vacuum being applied for establishing aspirated fluid flow;
 a flow measurement device configured to generate a signal indicative of the rate at which fluid flow is aspirated;
 a flow controller that monitors the vacuum sensor and the flow measurement device, and communicates a requested vacuum level to the vacuum device to establish a desired vacuum level, the flow controller being configured to implement a first feed back loop that compares the requested vacuum level with the actual sensed vacuum level and adjusts the requested vacuum to achieve the desired vacuum level, the flow controller being further configured to implement a second feedback loop that compares the sensed aspiration flow rate with a desired aspiration flow rate and adjusts the requested vacuum communicated to the vacuum device to achieve the desired aspirated fluid flow rate;
 a user command input device for enabling the input of a desired vacuum level, wherein the flow controller is configured to receive a desired vacuum level and to communicate a signal including a requested vacuum level to the vacuum device,
 wherein the vacuum device is configured to receive a signal from the flow controller that includes a requested vacuum level to be applied, and is further configured to receive signal information from the vacuum sensor indicative of the sensed vacuum level, and to generate a vacuum level based on the sensed vacuum level to achieve the requested vacuum communicated by the flow controller; and
 wherein the vacuum sensor provides an output signal indicative of the level of the vacuum being applied, which output signal is used to determine a time averaged vacuum signal based on periodic sampling of the output signal.

2. The aspiration flow control system of claim 1, wherein the vacuum device compares the sensed vacuum level information to the requested vacuum level, and increases or decreases the vacuum being applied to achieve the requested vacuum level.

3. The aspiration flow control system of claim 1, wherein the flow controller compares the sensed aspiration flow rate to a desired aspiration flow rate, and the flow controller adjusts the requested vacuum level communicated to the vacuum device to increase or decrease the vacuum being applied by the vacuum device, to thereby achieve the desired aspirated fluid flow rate.

4. The aspiration flow control system of claim 1, wherein the vacuum device is a venturi-based system in communication with a pressurized air source that supplies pressurized air to a venturi for establishing a vacuum level applied at a venturi port.

5. The aspiration flow control system of claim 1, wherein the vacuum level established by the venturi-based system is adjusted by a signal to a vacuum bleed valve that adjusts the communication of pressurized air to the venturi which varies the extent of bleed based on the signal, to thereby establish the requested vacuum level.

6. The aspiration flow control system of claim 1, wherein the vacuum device is a vacuum pump that generates a vacuum based on an electrical input to the pump, wherein the vacuum level established by the pump is adjusted by adjusting the electrical signal to the pump.

* * * * *